United States Patent [19]

Ohki et al.

[11] Patent Number: 5,619,985

[45] Date of Patent: Apr. 15, 1997

[54] INHALER TYPE MEDICINE ADMINISTERING DEVICE

[75] Inventors: Hisatomo Ohki; Shigemi Nakamura; Kazunori Ishizeki; Atsuo Wakayama, all of Atsugi; Akira Yanagawa, Yokohama, all of Japan

[73] Assignees: Unisia Jecs Corporation, Atsugi; Dott Limited Company, Yokohama, both of Japan

[21] Appl. No.: 510,850

[22] Filed: Aug. 3, 1995

[30] Foreign Application Priority Data

Aug. 8, 1994 [JP] Japan .................................. 6-206056

[51] Int. Cl.$^6$ .............................................. A61M 15/00
[52] U.S. Cl. ............................ 128/203.21; 128/203.15; 128/203.25
[58] Field of Search .................... 128/203.12, 203.15, 128/203.21, 203.23, 203.24

[56] References Cited

U.S. PATENT DOCUMENTS

| | | | |
|---|---|---|---|
| 2,517,482 | 8/1950 | Hall | 128/203.21 X |
| 2,609,817 | 9/1952 | Falcone | 128/203.23 |
| 2,641,254 | 6/1953 | Brown | 128/203.23 |
| 3,507,277 | 4/1970 | Altounyan et al. | 128/203.21 X |
| 3,837,341 | 9/1974 | Bell | 128/203.21 X |
| 3,918,451 | 11/1975 | Steil | 128/203.21 X |
| 4,013,075 | 3/1977 | Cocozza | 128/203.21 X |
| 4,105,027 | 8/1978 | Lundquist | 128/203.21 X |
| 4,889,114 | 12/1989 | Kladders | 128/203.15 |
| 4,995,385 | 2/1991 | Valentini et al. | 128/203.21 |
| 5,048,514 | 9/1991 | Ramella | 128/203.21 |

FOREIGN PATENT DOCUMENTS

| | | |
|---|---|---|
| 61599/90 | 4/1991 | Australia . |
| 0041783 | 12/1981 | European Pat. Off. . |
| 0147755 | 7/1985 | European Pat. Off. . |
| 0303844 | 2/1989 | European Pat. Off. . |
| 0525720 | 2/1993 | European Pat. Off. . |
| 6-185564 | 7/1994 | Japan . |
| 91/02558 | 3/1991 | WIPO . |

*Primary Examiner*—V. Millia
*Assistant Examiner*—Eric P. Raciti
*Attorney, Agent, or Firm*—Foley & Lardner

[57] ABSTRACT

An inhaler type medicine administering device for administering fine granular medicine to the lungs of a patent. The medicine admimistering device comprises a generally cylindrical inhaling piece including a cylindrical holder accommodating section. First and second outside pin insertion holes are formed through the cylindrical wall of the holder accommodating section. A capsule holder is provided to be accommodable within the holder accommodating section of the inhaling piece. The capsule holder is formed with a capsule accommodating hole opened to its end section in which hole a capsule containing medicine is accommodable. First and second inside pin insertion holes are formed extending in the diametrical direction of the capsule holder so as to pass through the capsule accommodating hole. The first inside pin insertion hole is capable of being brought into alignment with the first outside pin insertion hole to form a first pin insertion hole. The second inside pin insertion hole is capable of being brought into alignment with the second outside pin insertion hole to form a second pin insertion hole. An inflow-side passage is located radially outward of the capsule accommodating hole and has a first open end opened at the one end section of the capsule holder, and a second open end connected with the first inside pin insertion hole. An outflow-side passage is located radially outward of the capsule accommodating hole and connects the inside second pin insertion hole to the inhaling opening. Additionally, a perforator is provided including first and second pins which are insertable respectively into the first and second pin insertion holes in order to form holes in the capsule accommodated in the capsule accommodating hole.

12 Claims, 10 Drawing Sheets

INHALER TYPE MEDICINE ADMINISTERING DEVICE

BACKGROUND OF THE INVENTION

1. Field of Invention

This invention relates to improvements in an inhaler type medicine administering device suitable for, for example, administering granular medicine into the lungs of a patient under breathing-in action of the patient.

2. Description of the Prior Art

In general, administrating a medicine into the lungs of an asthma patient or the like is carried out, for example, in a manner of injecting the medicine to the patient, in a manner that the patent inhales the medicine by using a liquid aerosol sprayer, in a manner that the patent inhales fine and granular medicine (having a grain size, for example, ranging from 5 to 10 μm) filled in a capsule by breaking the capsule.

Of these administering manners, the above manner that the patient inhales fine and granular medicine filled in the capsule by breaking the capsule is extensively employed because of readiness. This manner is usually accomplished as follows: The asthma patient holds an inhaler in hand and installs the capsule containing the granular medicine into the inhaler. Then, the patient breaks the capsule by making a hole in the capsule with a needle and inhales the medicine through an inhaling opening of the inhaler.

However, difficulties have encountered in the above conventional medicine administering manner using the capsule, in which granular medicine unavoidably adheres to the wall surface of an air flow passage of the inhaler through which passage air stream is inhaled together with the medicine, because the conventional inhaler is not arranged suitable in a manner of introducing the air stream from a medicine ejection section through an inhaling passageway of the inhaler which passageway leads to the mouth of the patient. Additionally, the outflow-side air passage is not suitable in shape and therefore is unavoidably clogged with breaking pieces of the capsule when openings are formed in the capsule.

SUMMARY OF THE INVENTION

It is an object of the present invention is to provide an improved inhaler type medicine administering device which can effectively overcome drawbacks encountered in conventional inhaler type medicine administering devices.

Another object of the present invention is to provide an improved inhaler type medicine administering device by which medicine can be effectively administered into the lungs of a patient while preventing the medicine from adhering to the inner wall surface of an air flow passageway of the device through which air flows together with the medicine toward the mouth of the patient.

A further object of the present invention is to provide an improved inhaler type medicine administering device which is arranged to effectively generate an air stream which passes through a medicine capsule accommodated in the medicine administering device, which air stream can effectively carry the medicine to the mouth of the patient while uniformly dispersing the medicine into the air stream.

An aspect of the present invention resides in a medicine administering device comprising a main body which is formed with an inhaling opening through which granular medicine is administered into a human body. A chamber for accommodating the granular medicine is formed in the main body. The main body is formed with an air inflow passage through which the chamber is in communication with atmospheric air, air being introduced through the air inflow passage into the chamber to be mixed with the granular medicine, and an air outflow passage through which the chamber is in communication with the inhaling opening, air mixed with the granular medicine being introduced through the air outflow passage to the inhaling opening. The main body is further formed with a cutout formed to be connected to a downstream side of the air outflow passage, the downstream side being in communication with the inhaling opening.

Another aspect of the present invention resides in an inhaler type medicine administering device comprising a main body having first and second end sections which are axially opposite. The main body is formed with a capsule accommodating hole opened to the first end section. A capsule containing medicine is accommodable in the capsule accommodating hole. An inhaling opening is opened to the second end section. First and second pin insertion holes are formed extending in a diametrical direction of the main body so as to pass through the capsule accommodating hole. Each pin insertion hole has first and second sections which are located respectively at opposite sides of axis of the capsule accommodating hole. An air flow passage is located radially outward of the capsule accommodating hole and has a first end opened to the first end section of the main body and located near the capsule accommodating hole, and a second end opened to be in communication with the inhaling opening, the air flow passage extending through the capsule accommodating hole and through the first and second pin insertion holes. Additionally, a perforator is provided including first and second pins which are insatiable respectively into the first and second pin insertion holes to form holes in the capsule accommodated in the capsule accommodating hole.

According to the above aspect, first the capsule is accommodated in the capsule accommodating hole of the main body of the medicine administering device. Then, the pins of the perforator are inserted respectively into the pin insertion holes of the main body thereby forming holes in the capsule containing the medicine. As a result, the air flow passage is formed through the first and second pin insertion holes and the capsule with the holes. When the patient breathes in to inhale the medicine in this condition, air stream flows through the air flow passage and therefore flows through the first pin insertion hole, the capsule, the second pin insertion hole in the order mentioned and then drawn through the inhaling opening of the medicine administering device into the mouth of the patient. Thereafter, the medicine is drawn through the asthma to the lungs of the patient. During this process, when air stream enters and flows through the inside the capsule, the medicine within the capsule can be effectively agitated and dispersed into the air stream, so that the medicine can be effectively administered into the lungs.

Optionally, the main body of the medicine administering device of the above aspect is formed with an outflow passageway which is formed inside the main body to connect the outflow-side passage to the inhaling opening, wherein a tapered surface is formed in the outflow passageway in a manner to be tapered toward an upstream side of the outflow passageway to rectify air stream flowing from the second end of the air flow passage through the outflow passageway to the inhaling opening. By virtue of this tapered surface formed situated to the outflow passageway of the main body, drastic rolling-up of air stream can be prevented from occurring in the outflow passageway immediately upstream of the capsule, thereby rectifying the air stream flowing through the outflow passageway and directing to the inhaling opening in contact with the mouth of the patient. This effectively prevents the medicine from adhering to the inside wall surface of the main body of the medicine administering device.

A further aspect of the present invention resides in an inhaler type medicine administering device comprising a main body having first and second end sections which are axially opposite. The main body is formed with a capsule accommodating hole opened to the first end section. A capsule containing medicine is accommodable in the capsule accommodating hole. An inhaling opening is opened to the second end section. First and second pin insertion holes are formed extending in a diametrical direction of the main body so as to pass through the capsule accommodating hole, each pin insertion hole having first and second sections which are located respectively at opposite sides of axis of the capsule accommodating hole. An inflow-side passage is located radially outward of the capsule accommodating hole and has a first open end opened at the first end-section of the main body, and a second open end connected with the first pin insertion hole. An outflow-side passage is located radially outward of the capsule accommodating hole and connecting the second pin insertion hole to the inhaling opening. Additionally, a perforator is provided including first and second pins which are insertable respectively into the first and second pin insertion holes to form holes in the capsule accommodated in the capsule accommodating hole.

According to the above aspect, the whole amount of air flowing into the inflow-side passage can be passed through the inside of the capsule, and therefore high speed air stream is generated through the inside of the capsule thereby effectively dispersing the medicine into the air stream while effectively carrying the medicine to the lungs of the patient. By this, it is made possible that an effective administration of the medicine can be accomplished even by a patient who is less in capacity of the lungs.

A further aspect of the present invention resides in an inhaler type medicine administering device comprising a generally cylindrical inhaling piece having first and second end sections which are axially opposite. The inhaling piece includes a cylindrical holder accommodating section located near the first end section of the inhaling piece, and is formed with first and second outside pin insertion holes formed through a cylindrical wall of the holder accommodating section. An inhaling opening is opened to the second end section of the inhaling piece. A capsule holder is provided to be accommodable within the holder accommodating section of the inhaling piece. The capsule holder has first and second end sections which are opposite to each other. The capsule holder section is formed with a capsule accommodating hole opened to the first end section of the capsule holder. A capsule containing medicine is accommodable in the capsule accommodating hole. First and second inside pin insertion holes are formed extending in a diametrical direction of the capsule holder so as to pass through the capsule accommodating hole. Each inside pin insertion hole has first and second sections which are located respectively at opposite sides of axis of the capsule accommodating hole. The first inside pin insertion hole is capable of being brought into alignment with the first outside pin insertion hole to form a first pin insertion hole. The second inside pin insertion hole is capable of being brought into alignment with the second outside pin insertion hole to form a second pin insertion hole. An inflow-side passage is located radially outward of the capsule accommodating hole and has a first open end opened at the first end section of the capsule holder, and a second open end connected with the first inside pin insertion hole. An outflow-side passage is located radially outward of the capsule accommodating hole and connects the inside second pin insertion hole to the inhaling opening. Additionally, a perforator is provided including first and second pins which are insertable respectively into the first and second pin insertion holes to form holes in the capsule accommodated in the capsule accommodating hole.

According to the above aspect, the main body of the medicine administering device is constituted of the inhaler piece and the capsule holder to be supplied with the medicine capsule. The inhaler piece and the capsule holder are detachable or separable from each other, and therefore cleaning of the main body is largely facilitated to remove the medicine adhered to the inside of the main body.

BRIEF DESCRIPTION OF THE DRAWINGS

In the drawings, like reference numerals designate like parts and elements throughout all figures, in which:

FIG. 1 is an exploded perspective view of an embodiment of an inhaler type medicine administering device according to the present invention;

FIG. 2 is a vertical sectional view of an inhaler piece of the medicine administering device of FIG. 1;

FIG. 3 is a bottom plan view of the inhaler piece of FIG. 2;

FIG. 4 is a vertical sectional view of a capsule holder of the medicine administering device of FIG. 1, taken in the direction of arrows substantially along the line IV—IV of FIG. 6;

FIG. 5 is a vertical sectional view of the capsule holder of FIG. 4, taken in the direction of arrows substantially along the line V—V of FIG. 6;

FIG. 6 is a top plan view of the capsule holder of FIGS. 4 and 5;

FIG. 7 is a vertical sectional view of a main body of the medicine administering device of FIG. 1 including the incorporated inhaler piece and capsule holder, showing a state where a capsule is to be accommodated in the capsule holder;

FIG. 8 is a vertical sectional view of the medicine administering device of FIG. 1, showing a state where pins of a perforator are to be inserted into pin insertion holes of the inhaling piece after the capsule is accommodated in the capsule holder;

FIG. 9 is a vertical sectional view of the medicine administering device of FIG. 1, showing a state where the pins of the perforator have been inserted respectively into the pin insertion holes of the main body of the medicine administering device thereby forming holes in the capsule;

FIG. 10 is an enlarged vertical sectional view of an essential part of the medicine administering device of FIG. 1, illustrating air stream generated inside the medicine administering device when the medicine is inhaled;

FIG. 11 is a vertical sectional view of the main body of another embodiment of the inhaler type medicine administering device according to the present invention;

FIG. 12 is a vertical sectional view of a capsule holder of the main body of FIG. 11;

FIG. 13 is a vertical sectional view of an essential part of the medicine administering device of FIG. 11, illustrating air stream generated when the medicine is inhaled; and FIG. 14 is a vertical sectional view of the main body of a further embodiment of the inhaler type medicine administering device according to the present invention.

DETAILED DESCRIPTION OF THE INVENTION

Figure 1:
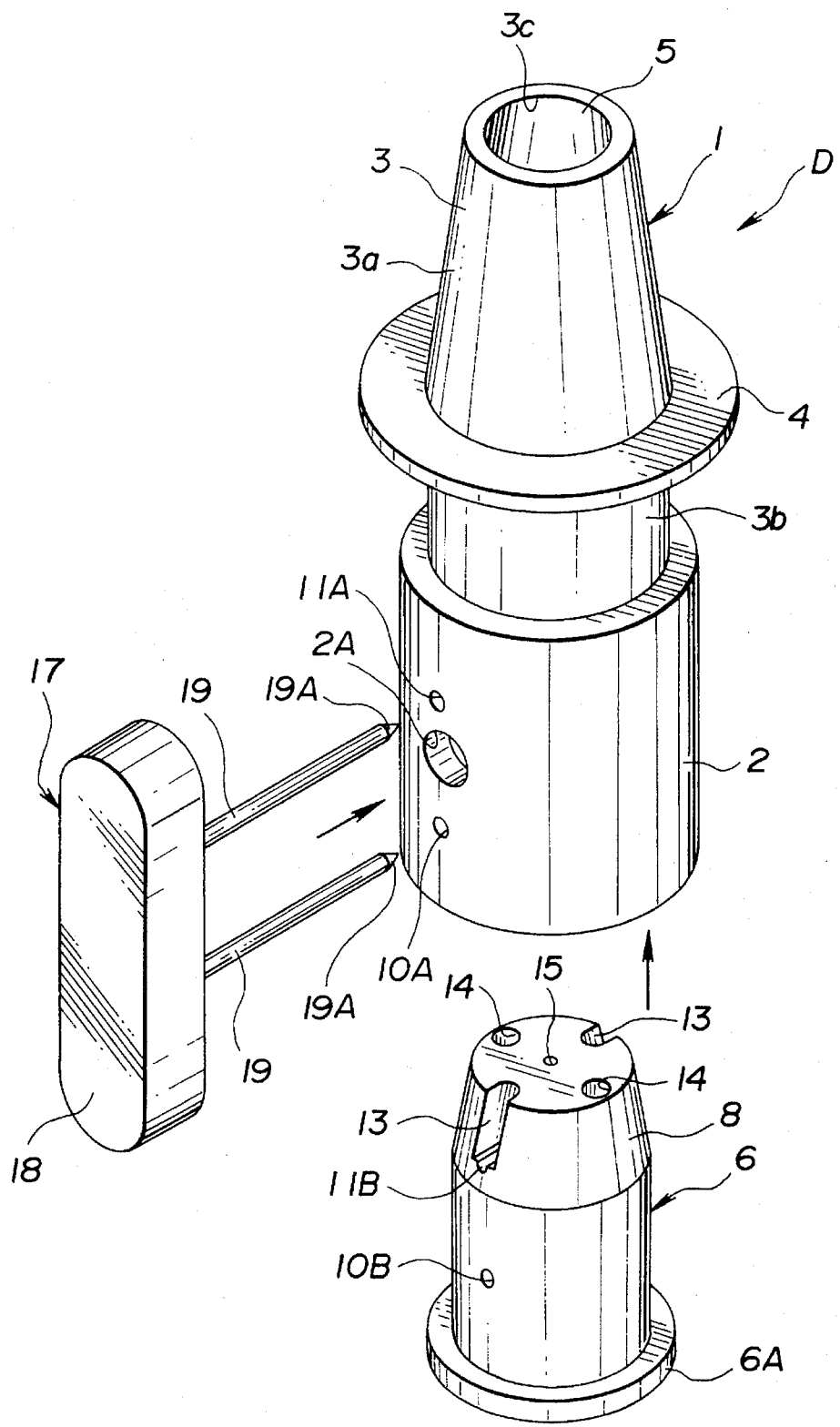
Figure 2:
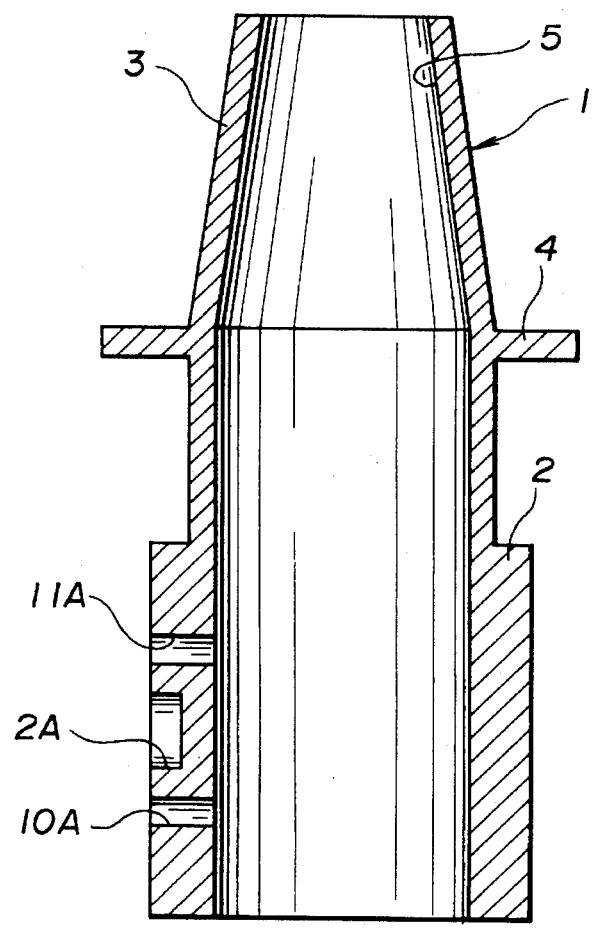
Figure 3:
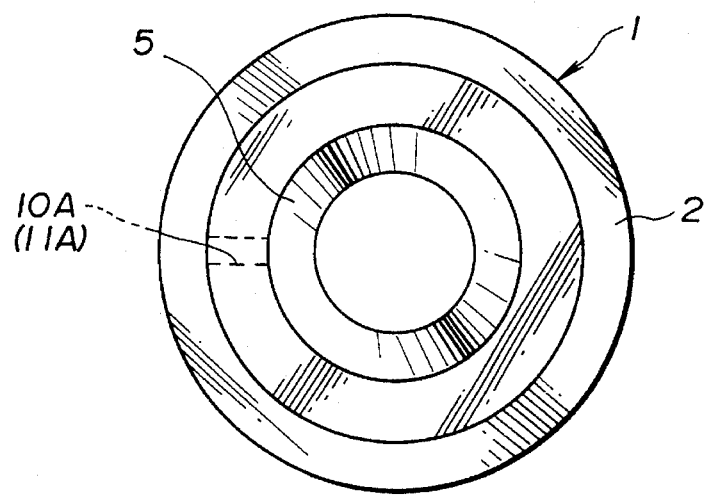

Referring now to FIGS. 1 to 10 of the drawings, an embodiment of an inhaler type medicine administering device according to the present invention is illustrated by the reference character D. The administering device D comprises an inhaling piece 1 which is formed generally cylindrical and made of a material approved by the Drugs, Cosmetics and Medical Instruments Act throughout the world. The inhaling piece 1 includes a holder accommodating section 2 which is located at an axially one end side (air inflow-side) of the inhaling piece 1 and has a wall thickness larger than other sections of the inhaling piece 1. The holder accommodating section 2 is adapted to hold therein a capsule holder 6 which will be discussed after. The inhaling piece 1 further includes an inhaling section 3 which is located at the other end side (air outflow-side) of the inhaling piece 1 and has tapered and cylindrical parts 3a, 3b.

The cylindrical part 3b is located between and integral with the tapered part 3a and the holder accommodating section 2. The tapered part 3a is formed tapered toward the extreme free end of the inhaling section 3 so that the tapered part 3a is in the shape of a frustoconical cylinder. The tapered part 3a is formed with an inside space which serves as an outflow passageway 5 through which air flows. A part of the outflow passageway 5 at the extreme free end serves as an inhaling opening 3c to be situated in the mouth of a patient. An annular flange section 4 is formed on the peripheral surface of the inhaling section 3 and extends radially outwardly. The flange section 4 is located between the tapered and cylindrical parts 3a, 3b of the inhaling piece 1. It will be understood that the air flow passageway 5 extends also through the inside of the holder accommodating section 2.

The holder accommodating section 2 is formed with outside pin insertion holes 10A, 10B which are located at a radial one side of the holder accomodating section 2. The outside pin insertion holes 10A, 11A are formed radially through the cylindrical wall of the holder accommodating section 2 and positioned axially separate from each other. The outside pin insertion holes 10A, 11A form part of respective pin insertion holes 10, 11 which will be discussed after. A circular depression 2A is formed at the outer peripheral surface of the holder accommodating section 2 to accommodate therein a spring 20, and located axially between the pin inserting holes 10A, 11A.

Figure 5:
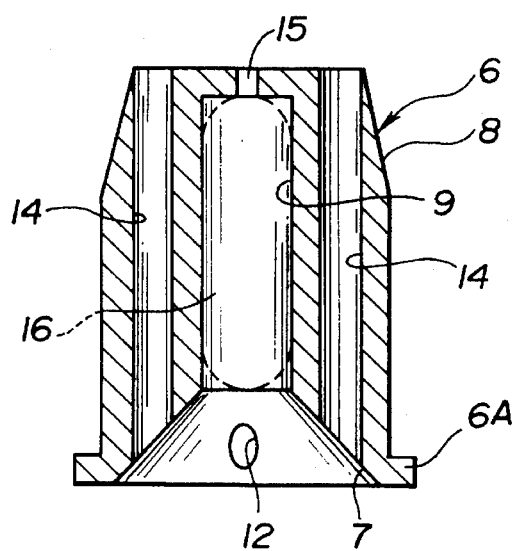
Figure 6:
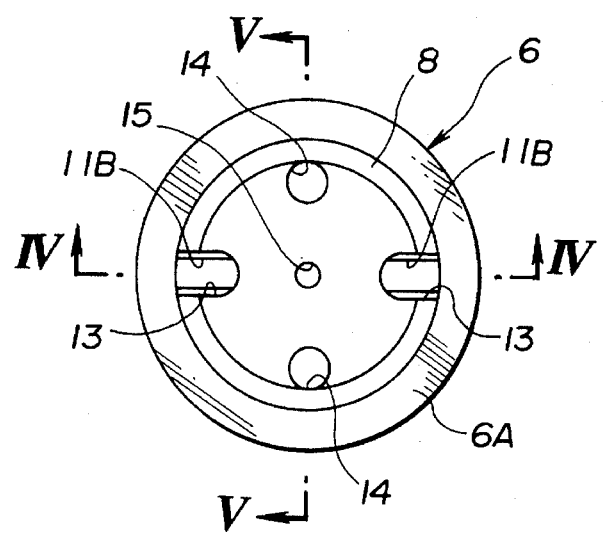

The capsule holder 6 is formed generally column-like and provided at its one (lower) end with an annular flange-like stopper portion 6A, so that the capsule holder 6 can be positioned relative to the holder accommodating section 2. The capsule holder 6 is formed with a capsule accommodating hole 9 which is coaxial with the capsule holder 6 and axially extends. The capsule holder 6 is formed at the end face of its one (lower) end section with a tapered inflow-side depression or opening 7 which connects or merges with the capsule accommodating hole 9 and has a diameter gradually decreasing toward the capsule accommodating hole 9. It will be understood that a capsule 16 is accommodated in the capsule accommodating hole 9 as shown in FIG. 5. The capsule 16 is formed long and generally cylindrical as usual and filled with fine and granular medicine (not shown).

Figure 4:
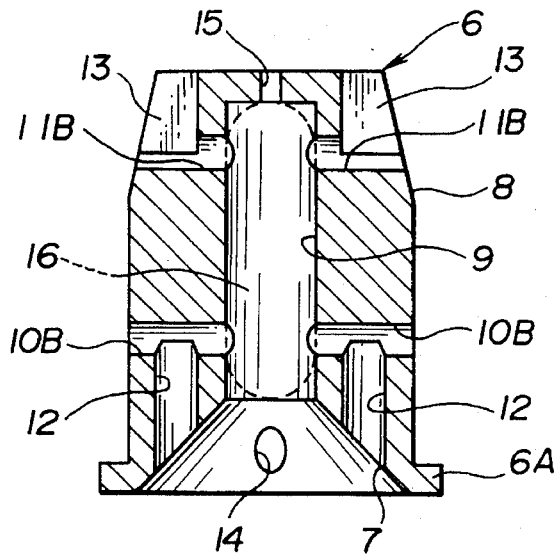

The capsule holder 6 is formed at the other (upper) end section with a outflow-side tapered or frustoconical surface 8 which are coaxial and contiguous with the outer peripheral surface of the capsule holder 6. The outflow-side tapered surface 8 extends from an axial peripheral position slightly lower than an inside pin insertion hole 11B, toward the upper end of the capsule holder 6. The inside pin insertion hole 11B forms part of the pin insertion hole 11 and extends diametrically in a manner to pass through the capsule accommodating hole 9. Two outflow-side passages 13, 13 are formed to merge respective with the opposite end sections of the inside pin insertion hole 11B which opposite end sections are located at the opposite sides of the capsule accommodating hole 9. Each outflow-side passage 13 extends radially outwardly and axially upwardly as shown in FIG. 4 so as to open at both the upper end of face and the outflow-side tapered surface 8 of the capsule holder 6, thereby taking a groove shape. In other words, each outflow-side passage 13 is formed slit-like by cutting out a part extending from the tapered surface 8 to the inside pin insertion hole 11B, from the one (upper) end section of the capsule holder 6.

Another inside pin insertion hole 10B forming part of the pin insertion hole 10 is diametrically formed in the capsule holder 6, passing through the capsule accommodating hole 9. The opposite ends of the inside pin insertion hole 10B are formed at the cylindrical peripheral surface and positioned at opposite sides of the axis of the capsule holder 6.

Figure 7:
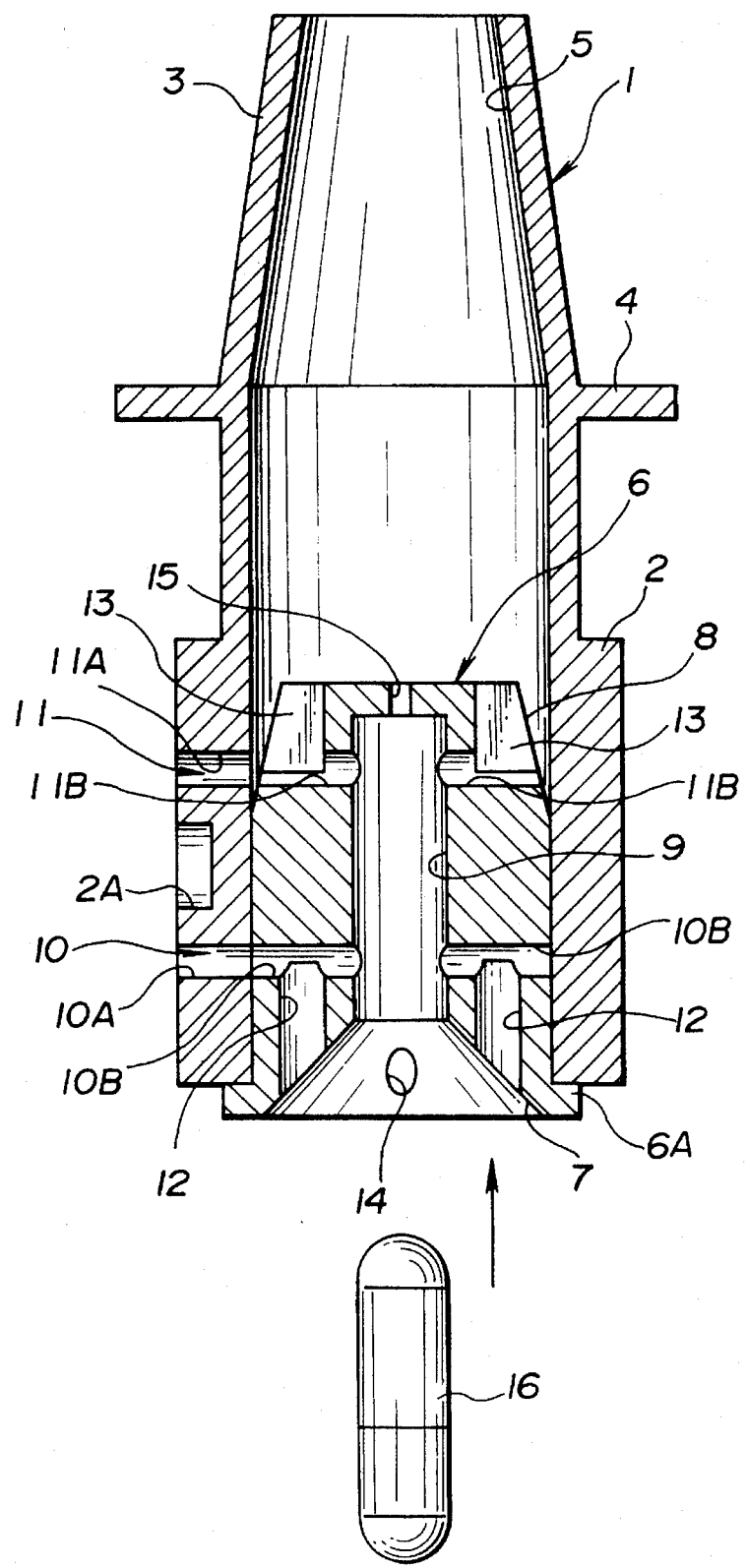

As shown in FIG. 7, the inflow-side and outflow-side pin insertion holes 10, 11 are formed extending diametrically throughout the wall of the holder accommodating section 2 of the inhaling piece 1 at the radial one side and the capsule holder 6. The inflow-side and outflow-side pin insertion holes 10, 11 are located axially separate from each other. The inflow-side pin insertion hole 10 includes the outside pin insertion hole 10A and the inside pin insertion hole 10B which are aligned with each other so that the hole 10 extends straight. The outflow-side pin insertion hole 11 includes the outside pin insertion hole 11A and the inside pin insertion hole 11B which are aligned with each other so that the hole 11 extends straight.

Two inflow-side passages 12, 12 are formed at the opposite sides of the axis of the capsule holder 6 in a manner to connect respectively with the opposite end sections of the inside pin insertion hole 10B which sections are located at the opposite sides of the capsule accommodating hole 9. Additionally, each inflow-side passage 12 connects with the tapered inflow-side opening 7 and extends in the axial direction of the capsule holder 6.

Two auxiliary air passages 14, 14 are formed axially in the capsule holder 6 in a manner to connect the tapered inflow-side opening 7 and the upper end face of the capsule holder 6 as shown in FIG. 5. The auxiliary air passages 14, 14 are located at the opposite sides of the capsule accommodating hole 9 and positioned such that their axis is separate from the axis of each pin insertion hole 10, 11 by an angle of 90 degrees in a peripheral direction as seen from FIG. 6. Each air passage 14 has the same diameter throughout its length.

The capsule holder 6 is formed with a small diameter hole 15 which opens at the upper end face of the capsule holder 6 and connects with the capsule accommodating hole 9. The hole 15 is arranged such that a part of a jig (not shown) is inserted through this hole 15 to remove the capsule 16 left in the capsule accommodating hole 9, after administration of the medicine by the patient has been completed.

Figure 9:
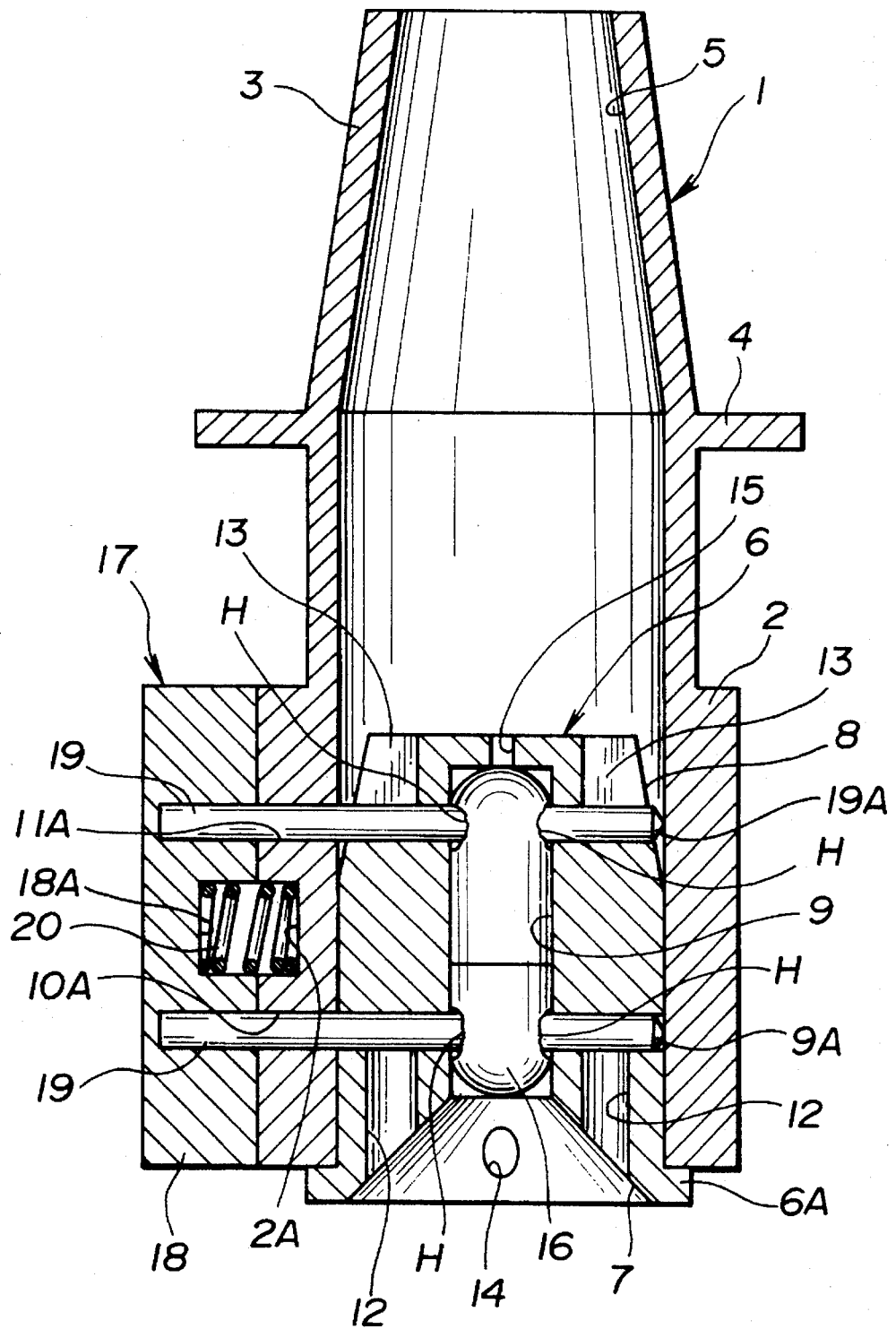

As shown in FIG. 1, a perforator 17 is provided as part of the inhaler type medicine administering device D and includes a support section 18 which is elongate in the axial direction of the inhaling piece 1. Two pins 19, 19 are fixed to the support section 18 and extend parallely vertically from the support section 18. The pins 19, 19 are separate from each other by a distance corresponding to that of the pin insertion holes 10, 11. Each pin 19 has a needle-like sharp tip end or piercing section 19A. When each pin 19 is inserted into the pin insertion hole 10 (11), the sharp tip end section 19A passes through the outside pin insertion hole 10A (11A), the end section of the inside pin insertion hole 10B (11B), the capsule accommodating hole 9, the other end section of the inside pin insertion hole 10B (11B) in the mentioned order and comes into contact with the inner surface of the holder accommodating section 2. Accordingly, each sharp tip end section 19A can form through-holes H in the capsule 16 without causing breakage of the capsule 16 as shown in FIG. 9 when the tip end section 19A pierces the capsule 16 accommodated in the capsule accommodating hole.

The support section 18 of the perforator 17 is formed with an annular groove 18A located corresponding to the annular groove 2A in the holder accommodating section 2. The spring 20 is held in the depression 2A and serves to cause the tip end section 19A of each pin 19 to return to its position within the outside pin insertion hole 10A (11A) of the holder accommodating section 2, after the through-holes H are formed in the capsule 16.

The manner of operation of the thus arranged inhaler type medicine administering device D will be discussed hereinafter with reference to FIGS. 7 to 10.

First, the capsule holder 6 is inserted into the holder accommodating section 2 of the inhaler piece 1 from the one (lower) end side of the inhaler piece 1 and pushed until the stopper section 6A comes to contact with the one (lower) end of the holder accommodating section 2. At this time, the outside pin insertion hole 10A formed in the inhaler piece 1 is brought into alignment with the inside pin insertion hole 10B formed in the capsule holder 6 thereby forming the inflow-side pin insertion hole 10, while the outside pin insertion hole 11A is brought into alignment with the inside pin insertion hole 11B thereby forming the outflow-side pin insertion hole 11.

In this state, as shown in FIG. 7, the capsule 16 is inserted into the capsule accommodating hole 9 from the one (lower) end of the hole 9 so that the capsule 16 is located in position within the capsule accommodating hole 9. It will be understood that the capsule holder 6 is formed at its one (lower) end face with the inflow-side depression 7 which is tapered and merges with the capsule accommodating hole 9, and therefore the capsule 16 can be readily guided into the capsule accommodating hole 9.

Figure 8:
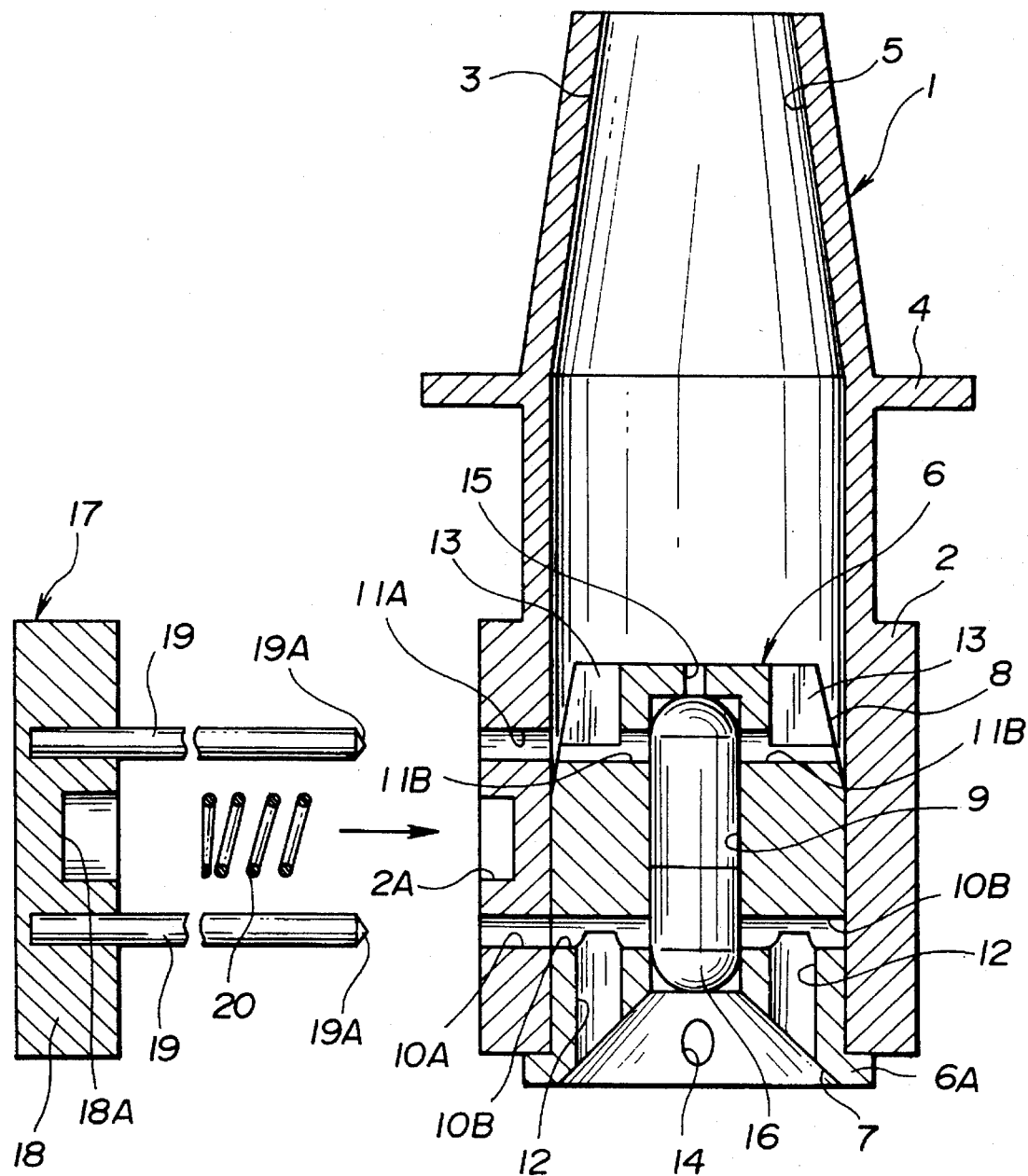

Subsequently, in a state where the capsule 16 has been accommodated in the capsule accommodating hole 9 as shown in FIG. 8, the pins 19, 19 of the perforator 17 are inserted respectively into the inflow and outflow-side pin insertion holes 10, 11 through the cylindrical side surface of the inhaling piece 1. Then, the sharp tip end section 19A of each pin 19 passes through the outside pin insertion hole 10A (11A), the end section of the inside pin insertion hole 10B (11B), the capsule accommodating hole 9, the other end section of the inside pin insertion hole 10B (11B) in the mentioned order and comes into contact with the inner surface of the holder accommodating section 2 as shown in FIG. 9. When the sharp tip end sections 19A of the respective pins 19 pass through the capsule accommodating hole 9, the four through-holes H, H, . . . are securely formed at the wall of the capsule 16 located in the capsule accommodating hole 9.

Figure 10:
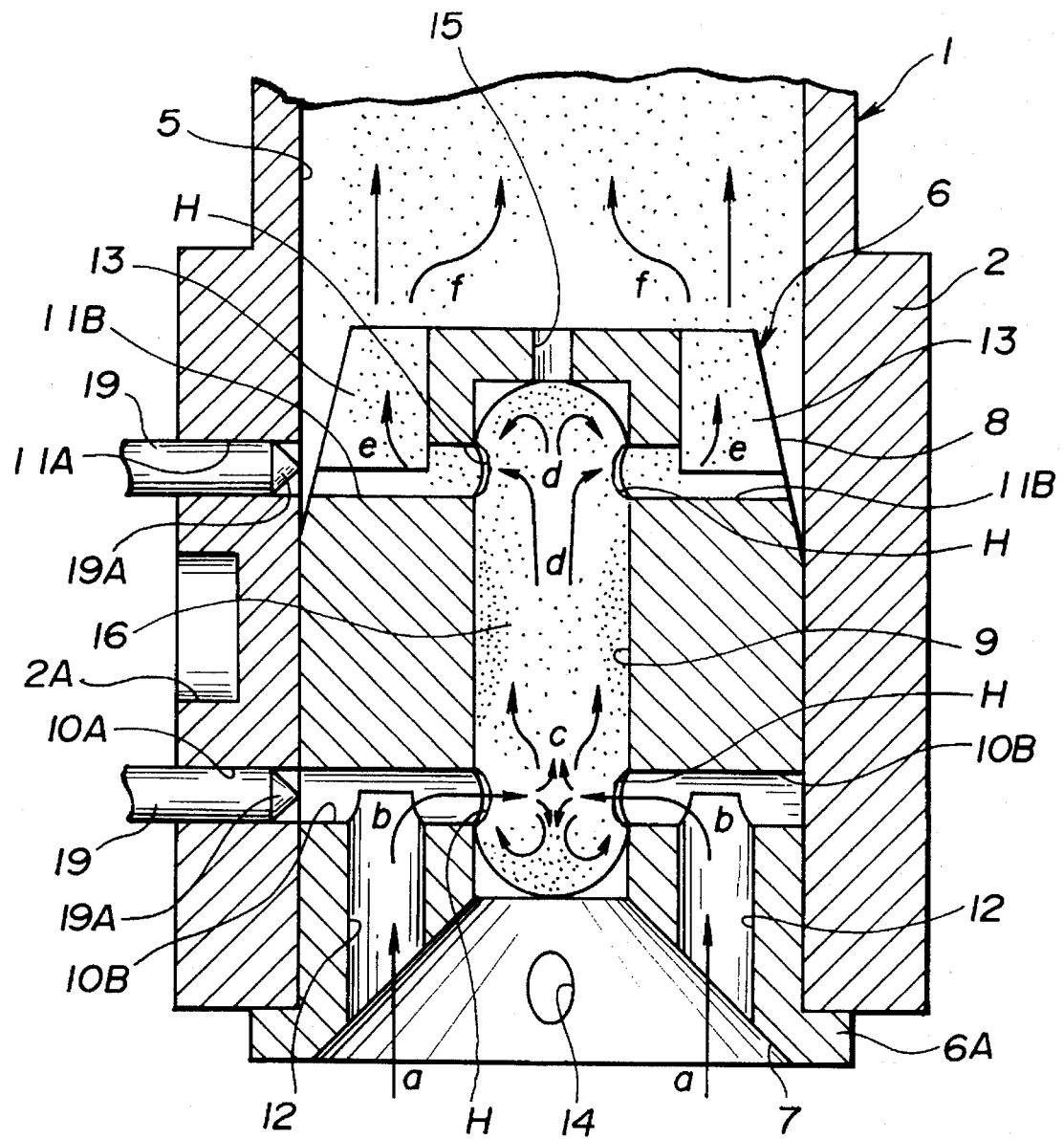
Figure 11:
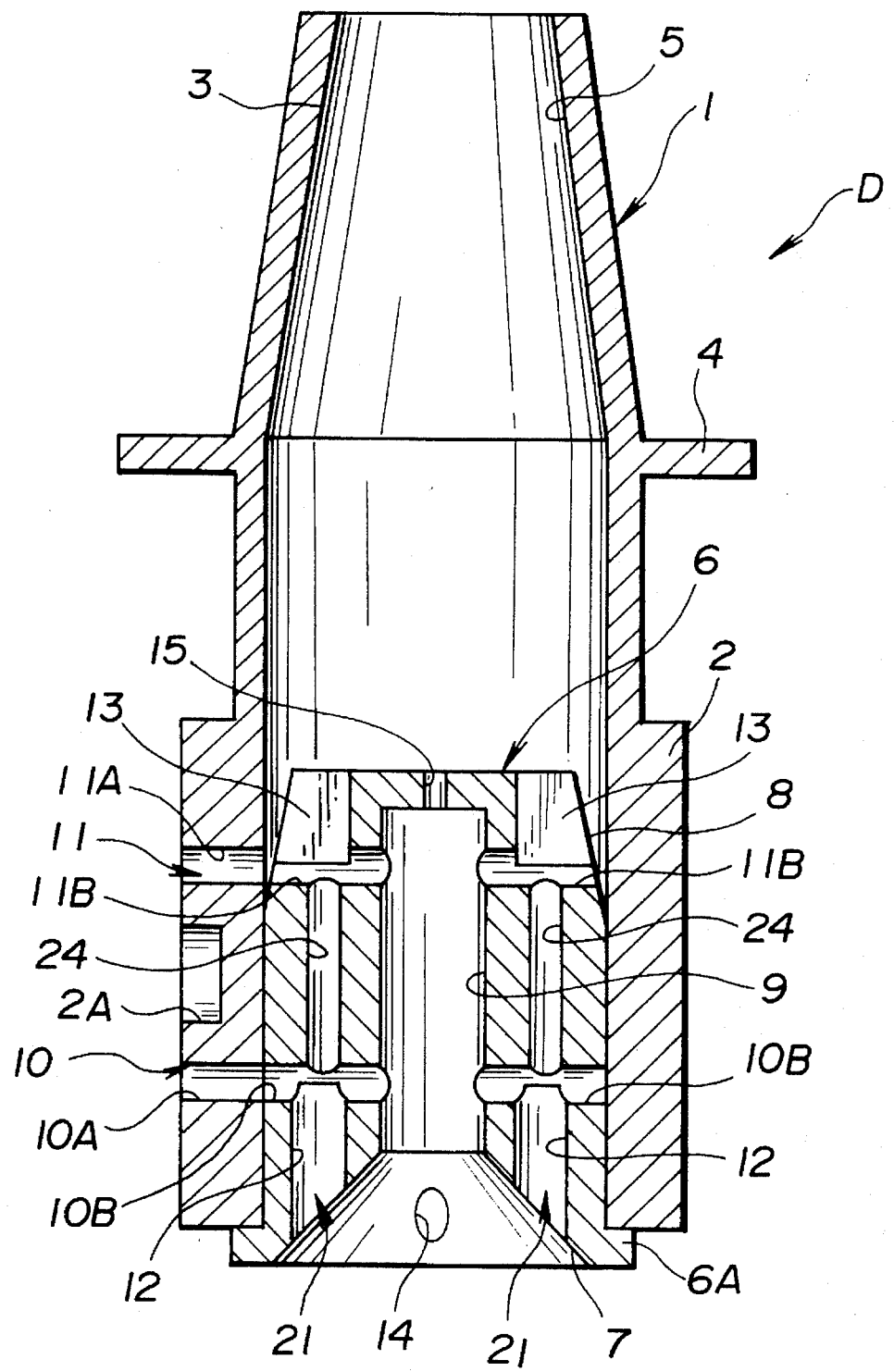
Figure 12:
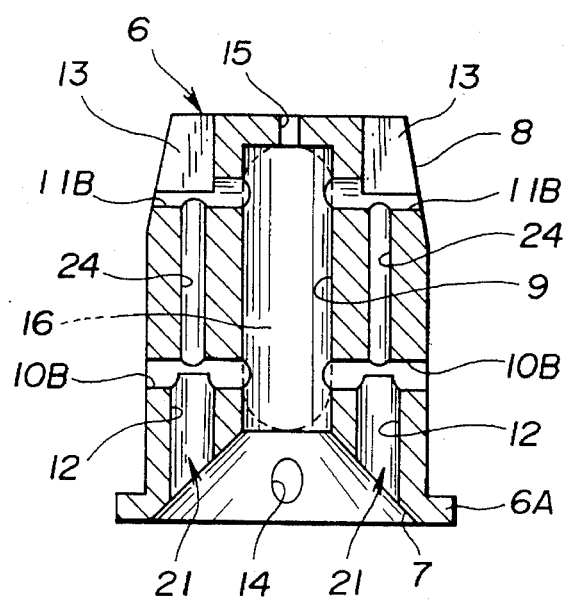
Figure 13:
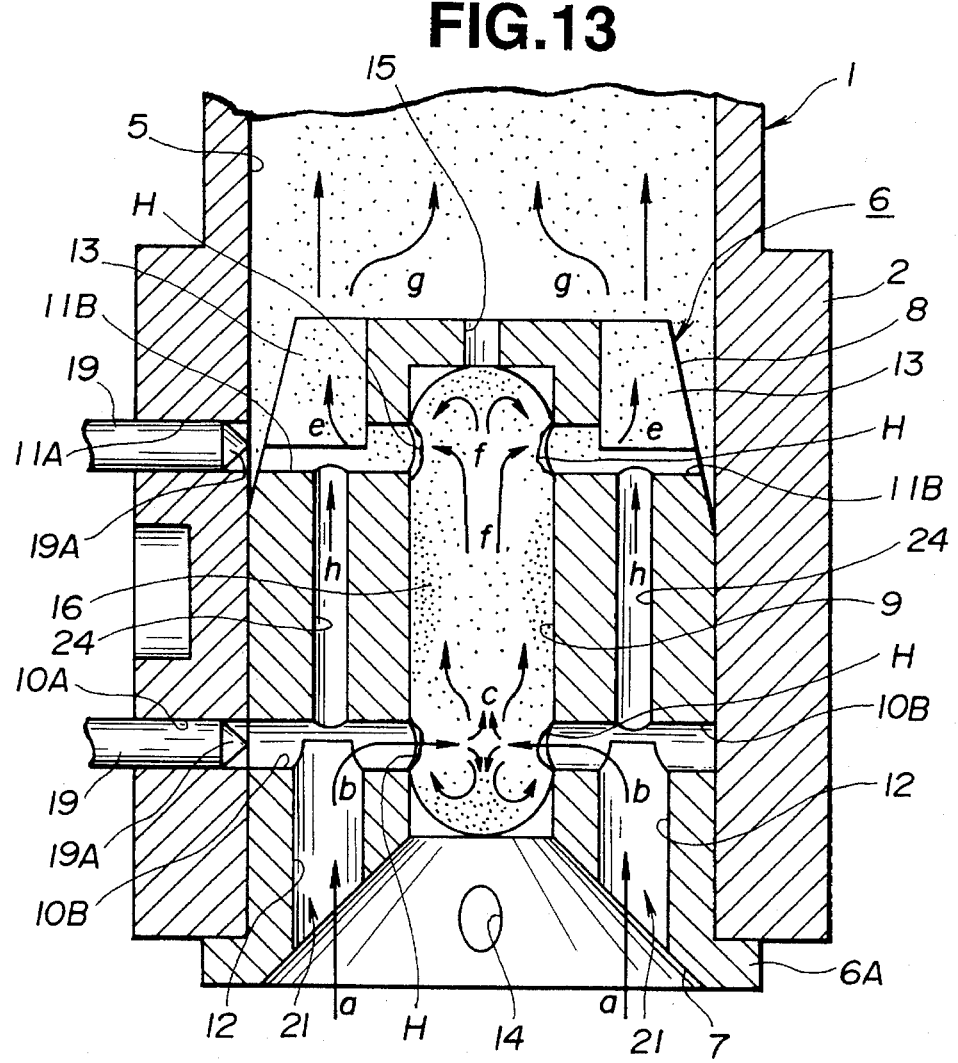

After the four through-holes H, H, . . . have been thus formed in the capsule 16, the respective pins 19 are returned to their positions as indicated in FIG. 10 under the biasing force of the spring 20, so that the tip end section 19A of each pin 19 is positioned within the outside pin insertion hole 10A (11A). before the patient inhales the medicine in the capsule 16.

When the patient holds in hand the inhaling section 3 of the inhaling piece 1 and breathes in to inhale the medicine, air is flown through the inflow-side depression 7 into inside of the inhaler type medicine administering device D to form air stream. The air stream passes through the auxiliary air flow passages 14, 14 in the direction from their one (lower) end to the other (upper) end.

The air stream also passes through the inflow-side passages 12, 12. As shown in FIG. 10, the air stream is drawn in each inflow-side passage 12 in the direction indicated by an arrow a and flows into the inside pin insertion hole 10B in the direction indicated by an arrow b, so that two air streams flow radially inwardly into the capsule accommodating hole 9 from the opposite directions. These air streams penetrate into the capsule 16 through the through-holes H since the through-holes H have been already formed in the capsule 16.

At this time, the air streams penetrated into the capsule 16 in the direction indicated by the arrows a, a collide with each other within the capsule 16 thereby generating turbulent flow as indicated by arrows c, c within the capsule 16 because the inside pin insertion hole 10B is formed straight so that the opposite end sections (of the hole 10B) located at the opposite sides of the capsule accommodating hole 9 face to and are aligned with each other. It will be understood that the granular medicine within the capsule 16 is compulsorily agitated under the action of the turbulent flows indicated by the arrows c, c and therefore can be securely mixed with air so as to be uniformly distributed in the air stream.

The air streams to be flown out of the capsule 16 is indicated by arrows d, d and has an air flow amount corresponding to that of the air streams indicated by the arrows b, b, and therefore air streams indicated by arrows e, e are generated to flow through the inside pin insertion hole 11B and the outflow-side passage 13, 13. At this time, the medicine is mixed in the air streams indicated by arrows d, d within the capsule 16, and therefore the medicine from the capsule 16 is carried by the air streams indicated by the arrows e, e and by the air streams which are within the outflow passageway 5 (indicated by arrows f, f) and flow through the inside of the inhaling section 3 of the inhaling piece 1. Then, the thus carried medicine reaches to the inside of the lungs of the patient through the inside of the mouth and the trachea of the patient, so that the medicine mixed in air stream can be securely administered to the lungs.

It will be appreciated from the above that the inhaler type medicine administering device D of this embodiment offers the following significant advantages:

(a) The pin insertion holes 10, 11 are formed diametrically through the capsule holder 6 so that the pins 19 of the perforator 17 are insertable into the pin insertion holes 10, 11. Therefore, the through-holes H, H, . . . can be securely formed through the capsule 16 by the respective tip end sections 19A, 19A of the pins 19, 19, preventing the capsule 16 from breaking.

(b) Air drawn in the medicine administering device D through the respective inflow-side passages 12, 12 flow into the capsule accommodating hole 9 via the opposite end sections of the inside pin insertion hole 10B so that two opposite air streams flow respectively in the directions to collide to each other. As a result, turbulent flows of air are generated within the capsule under the action of the air streams in the inside pin insertion hole 10B, thereby effectively mixing the granular medicine into air stream. This can reduces the amount of the medicine to be left in the capsule thereby to improve a carrying efficiency of the medicine to the lungs of the patient.

(d) Air stream passing through the inside of the capsule holder 6 flows in the order of the inflow-side passages 12, 12, the inside pin insertion hole 10B, the capsule accommodating hole 9, the inside pin insertion hole 11B and the outflow-side passages 13, 13. Accordingly, whole air stream flowing in through the inflow-side passages 12, 12 pass through the inside of the capsule 16, and therefore generating sufficient air stream in the medicine administering device D can be securely accomplished even by old people and children who are low in capacity of the lungs or low in air inhaling amount at the inhaling section 3. Administration of the medicine in the capsule 16 can be securely achieved with only one breathing-in action of them.

(d) Each outflow-side passage 13 is formed in the shape of a cutout groove and located at the (upper) end section of the capsule holder 6 in a manner to open to the outflow-side tapered surface 8 and to merge with the inside pin insertion hole 11B. Therefore, the inside pin insertion hole 11B and the outflow-side passage 13 can be effectively prevented from being clogged with broken pieces which are produced when the through-holes H are formed in the capsule 16.

(e) The capsule holder 6 is formed at its outflow-side peripheral surface with the outflow-side tapered surface 8. As a result, the stream of air inhaled through the inhaler section 3 of the inhaler piece 1 is rectified or smoothened. Additionally, under the action of combination of the above groove-shaped outflow-side passages 13, 13, the powder distribution of the medicine within the inhaling section 3 of the inhaling piece 1 can be uniformalized thereby making possible to inhale the medicine more effectively.

(f) The inhaling piece 1 and the capsule holder 6 are arranged to be detachable or separable from each other, and therefore cleaning of the medicine administrating device D can be easily accomplished to remove breaking pieces produced during formation of the through-holes H in the capsule 16 and to remove the medicine adhered to and left in the device D. Additionally, the capsule 16 can be easily removed from the capsule accommodating hole 9 of the capsule holder 6 by inserting the part (such as a needle) of the jig.

(g) The capsule holder 6 is formed with the auxiliary air flow passages 14, 14 extending axially, and therefore independent air stream can be formed separately from air stream which is formed in the inflow-side passages 12 and contains therein the medicine. As a result, the patient can breathe in much air as compared with a case of breathing in air only through the inflow-side passages 12, thereby lightening the patent's burden when the patient inhales the medicine by using the medicine administering device D.

FIGS. 11 to 13 illustrate another embodiment of the inhaler type medicine administering device D according to the present invention, which is similar to the embodiment of FIGS. 1 to 10 with the exception that the inflow-side passage

12, 12 are connected with the corresponding outflow-side passages 13, 13 through orifice or restrictor passages 24, 24, respectively.

More specifically, in this embodiment, the inflow-side passages 12, 12 are connected respectively with the opposite end sections (located at the opposite sides of the capsule accommodating hole 9) of the inside pin insertion hole 10B. Additionally, the opposite end sections of the inside pin insertion hole 10B are communicated respectively with the outflow-side passages 13, 13 through the orifice passages 24, 24. Each inflow-side passage 12, each orifice passage 24 and each outflow passage 13 constitutes an air flow passage 21 which extends in the direction of the axis of the capsule holder 6. As shown, each orifice passage 24 is arranged to be in coaxial alignment with the corresponding inflow passage 12. Each orifice passage 24 is smaller in diameter or cross-sectional area than that of each inflow-side passage 22 and of each outflow-side passage 13. In this embodiment, each outflow-side passage 13 is formed in the shape of a slit-like cutout groove and located at the (upper) end section of the capsule holder 6 in a manner to open to the outflow-side tapered surface 8 and to merge with the inside pin insertion hole 11B.

With this arrangement, when the patient holds in hand the inhaling section 3 of the inhaling piece 1 and breathes in to inhale the medicine, air is flown through the inflow-side depression 7 into the inhaler type medicine administering device D to form air stream. The air stream passes through the auxiliary air flow passages 14, 14 in the direction from their one (lower) end to the other (upper) end. The air stream also passes through the inflow-side passages 12, 12. As shown in FIG. 13, the air stream diverges into two streams which respectively flow into the inside pin insertion hole 10A and into the orifice passage 24 as indicated by arrows b, h. The air streams indicated by the arrows b, b are drawn into the capsule accommodating hole 9 and penetrate into the capsule 16 through the through-holes H since the through-holes H have been already formed in the capsule 16.

At this time, the air streams penetrated into the capsule 16 in the direction indicated by the arrows b, b collide with each other within the capsule 16 thereby generating turbulent flow as indicated by the arrows c, c. within the capsule 16 because the inside pin insertion hole 10B is formed straight so that the opposite end sections (of the hole 10B) located on the opposite sides of the capsule accommodating hole 9 face to and are aligned with each other. It will be understood that the granular medicine within the capsule 16 is compulsorily agitated under the action of the turbulent flows indicated by the arrows c, c and therefore can be securely mixed with air so as to be uniformly distributed in the air stream.

The air streams to be flown out of the capsule 16 is indicated by the arrows f, f and has an air flow amount corresponding to that of the air streams indicated by the arrows b, b thereby forming an outflow air stream exhibiting a high medicine discharging effect. Additionally, the air streams (indicated by the arrows h, h) flowing through the respective orifice passages 24, 24 compulsorily generate the air streams (indicated by the arrows e, e) each of which flows through each end section of the inside pin insertion hole 11B and the outflow-side passage 13. At this time, the medicine is mixed in the air streams indicated by arrows f, f within the capsule 16, and therefore the medicine from the capsule 16 is carried by the air streams indicated by the arrows e, e and then by the air streams which are within the outflow passageway 5 and indicated by the arrows g, g and moves through the inside of the inhaling section 3 of the inhaling piece 1. Then, the thus carried medicine reaches to the inside of the lungs of the patient through the inside of the mouth and the trachea of the patient, so that the medicine mixed in air stream can be securely administered to the lungs.

Thus, according to this embodiment, by virtue of providing the orifice passages 24, 24 in the inhaler type medicine administering device D, air stream drawn from each inflow-side passages 12 can be diverged into two air streams which are respectively directed into the inside pin insertion hole 10B and toward each orifice passage 24. At this time, by virtue of the fact that the diameter of the orifice passage 24 is smaller than the inside pin insertion hole 10B, air stream can be preferentially flown through the inside pin insertion hole 10B. As a result, the medicine within the capsule 16 can be securely carried to the upstream side in the medicine administering device D as same as the embodiment of FIGS. 1 to 10.

Figure 14:
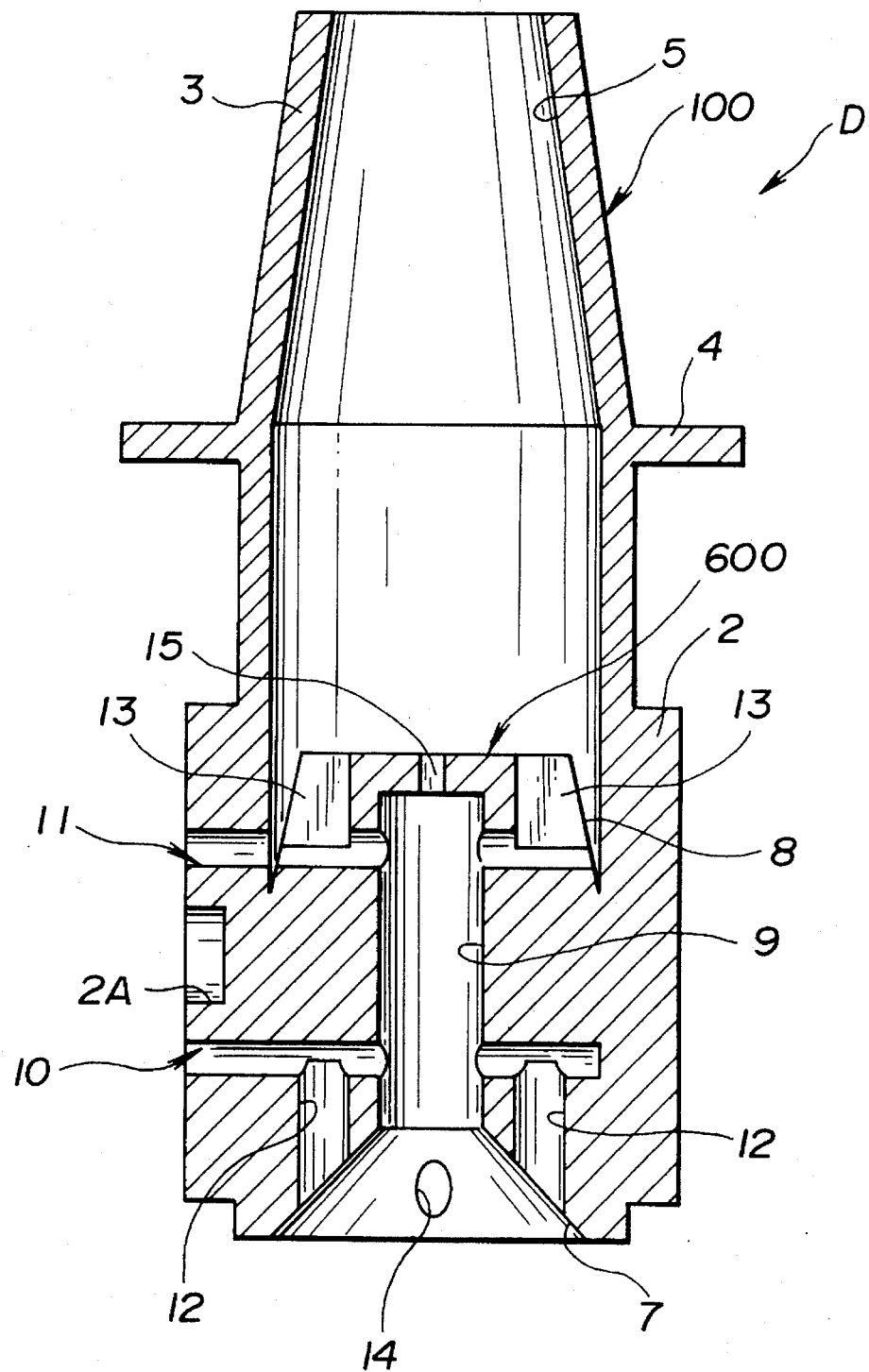

FIG. 14 illustrates a further embodiment of the inhaler type medicine administering device D according to the present invention, which is similar to the embodiment of FIGS. 1 to 10 with exception that the inhaling piece 1 and the capsule holder 6 are formed integral with each other as a one-piece structure. More specifically, in this embodiment, a capsule holder part 600 corresponding to the capsule holder 6 in the embodiment of FIGS. 1 to 10 is formed integral with an inhaling piece part 100 corresponding to the inhaling piece 1 of the embodiment of FIGS. 1 to 10.

It will be appreciated that the medicine administering device D of this embodiment can offer the same advantageous effects as those in the embodiment of FIGS. 1 to 10 except for the beforementioned effect at item (f).

While two medicine carrying passages (including two inflow passages 12, 12 and two outflow passages 13, 13) and two auxiliary air flow passages 14, 14 have been shown and described in the above-discussed embodiments, it will be understood that the number of the inflow passage 12, the outflow passage 13, and the auxiliary air flow passage 14 may not be two and therefore the number may be adjustable to be one, four or the like according to suction force of the patient who uses the inhaler type medicine administering device D, or otherwise the auxiliary air flow passage 14 may be omitted.

What is claimed is:

1. An inhaler type medicine administering device comprising:
   a main body having first and second end sections which are axially opposite, said main body including
      means defining a capsule accommodating hole opened to the first end section for accommodating a capsule containing medicine,
      means defining an inhaling opening opened to the second end section,
      means defining first and second pin insertion holes formed extending in a diametrical direction of said main body so as to pass through said capsule accommodating hole, each pin insertion hole having first and second sections which are located respectively at opposite sides of axis of said capsule accommodating hole, and
      means defining an air flow passage located radially outward of said capsule accommodating hole and having a first end opened to said first end section of said main body and located near said capsule accommodating hole, and a second end opened to be in communication with said inhaling opening, said air flow passage extending through said capsule accommodating hole and through said first and second pin insertion holes; and
   a perforator including first and second pins which are insertable respectively into said first and second pin insertion holes to form holes in the capsule accommodated in said capsule accommodating hole.

2. An inhaler type medicine administering device as claimed in claim 1, wherein said main body further includes means defining an outflow passageway which is formed inside the main body to connect said outflow-side passage to said inhaling opening, wherein said capsule accommodating hole defining means includes means defining a tapered surface which is located in said outflow passageway, said tapered surface being tapered toward an upstream side of said outflow passageway to rectify air stream flowing from said second end of said air flow passage through said outflow passageway to said inhaling opening.

3. An inhaler type medicine administering device comprising:
   a main body having first and second end sections which are axially opposite, said main body including
      means defining a capsule accommodating hole opened to the first end section for accommodating a capsule containing medicine,
      means defining an inhaling opening opened to the second end section,
      means defining first and second pin insertion holes formed extending in a diametrical direction of said main body so as to pass through said capsule accommodating hole, each pin insertion hole having first and second sections which are located respectively at opposite sides of axis of said capsule accommodating hole,
      means defining an inflow-side passage located radially outward of said capsule accommodating hole and having a first open end opened at the first end section of said main body, and a second open end connected with said first pin insertion hole, and
      means defining an outflow-side passage located radially outward of said capsule accommodating hole and connecting said second pin insertion hole to the inhaling opening; and
   a perforator including first and second pins which are insertable respectively into said first and second pin insertion holes to form holes in the capsule accommodated in said capsule accommodating hole.

4. An inhaler type medicine administering device as claimed in claim 3, wherein said main body further includes means defining an outflow passageway which is formed inside the main body to connect said outflow-side passage to said inhaling opening, wherein said capsule accommodating hole defining means includes means defining a tapered surface which is located in said outflow passageway and faces said inhaling opening, said outflow-side passage being formed through said tapered surface, said tapered surface being tapered toward an upstream side of said outflow passageway to rectify air stream flowing from said outflow-side passage through said outflow passageway to said inhaling opening.

5. An inhaler type medicine administering device comprising:
   a generally cylindrical inhaling piece having first and second end sections which are axially opposite, said inhaling piece including
      a cylindrical holder accommodating section located near said first end section of said inhaling piece,
      means defining first and second outside pin insertion holes formed through a cylindrical wall of said holder accommodating section, and means defining an inhaling opening opened to the second end section of said inhaling piece; and a capsule holder for receipt by said holder accommodating section of said inhaling piece, said capsule holder having first and second end sections which are opposite to each other and including means defining a capsule accommodating hole opened to the first end section of said capsule holder for accommodating a capsule containing medicine, means defining first and second inside pin insertion holes formed extending in a diametrical direction of said capsule holder so as to pass through said capsule accommodating hole, each inside pin insertion hole having first and second sections which are located respectively at opposite sides of axis of said capsule accommodating hole, said first inside pin insertion hole being capable of being brought into alignment with said first outside pin insertion hole to form a first pin insertion hole, said second inside pin insertion hole being capable of being brought into alignment with said second outside pin insertion hole to form a second pin insertion hole, means defining an inflow-side passage located radially outward of said capsule accommodating hole and having a first open end opened at the first end section of said capsule holder, and a second open end connected with said first inside pin insertion hole, and means defining an outflow-side passage located radially outward of said capsule accommodating hole and connecting said inside second pin insertion hole to the inhaling opening; and a perforator including first and second pins which are insertable respectively into said first and second pin insertion holes to form holes in the capsule accommodated in said capsule accommodating hole.

6. An inhaler type medicine administering device as claimed in claim 5, wherein said inflow-side passage defining means including means defining first and second inflow-side passages which are located at opposite sides of said capsule accommodating hole, the first open ends of said first and second inflow-side passages being respectively connected with the first and second sections of said first inside pin insertion hole.

7. An inhaler type medicine administering device as claimed in claim 5, wherein said capsule holder includes means defining a tapered surface which is formed at the second end section of said capsule holder and located in an outflow passageway which is defined inside said inhaling piece and located between said capsule holder and said inhaling opening of said inhaling piece, said outflow-side passage being formed through said tapered surface, said tapered surface being tapered toward an upstream side of said outflow passageway to rectify air stream flowing through said outflow passageway to said inhaling opening.

8. An inhaler type medicine administering device as claimed in claim 7, wherein said outflow-side passage defining means including means defining first and second outflow-side passages which are located at opposite sides of said capsule accommodating hole, the first open ends of said first and second outflow-side passages being respectively connected with the first and second sections of said first inside pin insertion hole, wherein each of said first and second outflow-side passages is formed groove-shaped and opened to said tapered surface of said capsule holder.

9. An inhaler type medicine administering device as claimed in claim 8, wherein said tapered surface of said capsule holder is a generally frustoconical surface.

10. An inhaler type medicine administering device as claimed in claim 5, wherein said inhaling piece further includes means defining an orifice passage through which said first and second inside pin insertion holes are connected with each other.

11. An inhaler type medicine administering device as claimed in claim 10, wherein said orifice passage defining means includes means for defining first and second orifice passages which are located at the opposite sides of said capsule accommodating hole, said first orifice passage being formed between the first section of said first inside pin insertion hole and the first section of said second inside pin insertion hole, said second orifice passage being formed between the second section of said first inside pin insertion hole and the second section of said second inside pin insertion hole.

12. An inhaler type medicine administering device as claimed in claim 10, wherein said orifice passage has a cross-sectional area smaller than that of said inflow-side and outflow-side passages.

* * * * *